US006531117B2

(12) United States Patent
Heger et al.

(10) Patent No.: US 6,531,117 B2
(45) Date of Patent: Mar. 11, 2003

(54) AQUEOUS DISPERSION OF WATER-INSOLUBLE ORGANIC UV FILTER SUBSTANCES

(75) Inventors: Robert Heger, Heidelberg (DE); Helmut Auweter, Limburgerhof (DE); Wilma M. Dausch, Limburgerhof (DE); Georg Konrad Zwissler, Heidelberg (DE); Thomas Wünsch, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/771,594

(22) Filed: Jan. 30, 2001

(65) Prior Publication Data

US 2001/0022965 A1 Sep. 20, 2001

(30) Foreign Application Priority Data

Feb. 17, 2000 (DE) .......................................... 100 07 116
Aug. 29, 2000 (DE) .......................................... 100 42 444

(51) Int. Cl.[7] .............................. A61K 7/42; A61K 9/44; B01F 3/08; B01F 3/12
(52) U.S. Cl. ........................... 424/59; 424/60; 424/401; 516/53; 516/77; 516/922; 516/923; 516/924
(58) Field of Search ............................. 424/401, 59, 60; 516/53, 97, 922, 923, 924

(56) References Cited

U.S. PATENT DOCUMENTS

| | | | | |
|---|---|---|---|---|
| 3,888,821 A | * | 6/1975 | Milford, Jr. ................. | 264/182 |
| 4,514,231 A | | 4/1985 | Kerner et al. ................ | 106/309 |
| 5,025,004 A | * | 6/1991 | Wu et al. .............. | 106/170.12 |
| 5,360,559 A | * | 11/1994 | Cooke ......................... | 252/8.61 |
| 6,303,281 B1 | * | 10/2001 | Wang et al. ................. | 430/507 |

FOREIGN PATENT DOCUMENTS

| | | |
|---|---|---|
| DE | 33 14 742 | 10/1984 |
| EP | 0 444 353 | 9/1991 |
| EP | 0 933 376 | 8/1999 |
| GB | 2 286 774 | 8/1995 |
| GB | 2 303 549 | 2/1997 |
| WO | WO 94/05645 | 3/1994 |

OTHER PUBLICATIONS

Deflandre et al. "Photostability assessment of sunscreens, Benzylidene camphor and dibenzoylmethane derivatives" International Journal of Cosmetic Science vol. 10 pp. 53–62 (1988).

* cited by examiner

Primary Examiner—Jose' G. Dees
Assistant Examiner—Marina Lamm
(74) Attorney, Agent, or Firm—Keil & Weinkauf

(57) ABSTRACT

The invention relates to aqueous dispersions of sparingly water-soluble or water-insoluble organic UV filter substances, which comprise at least one sparingly water-soluble or water-insoluble organic UV filter substance as colloidally disperse phase in amorphous or partially amorphous form.

31 Claims, No Drawings

AQUEOUS DISPERSION OF WATER-INSOLUBLE ORGANIC UV FILTER SUBSTANCES

The invention relates to aqueous dispersions of sparingly water-soluble or water-insoluble organic UV filter substances, to the preparation and further processing thereof to give dry powders, and to the use thereof as photostable light protection agents.

The quality and life of many organic materials, for example plastics and coating materials, but also pharmaceutical and cosmetic preparations, can be adversely affected by the action of light, in particular by UV rays. These losses in quality frequently become evident in the case of plastics and coating materials from yellowing, discoloration, cracking or embrittlement of the material. In the case of pharmaceutical and cosmetic preparations, the effect of UV rays can lead to the degradation of the active ingredients present in the formulations.

The harmful effect of the ultraviolet part of solar radiation on the skin or hair, which in the widest sense are also an organic material, is likewise a problem which is increasing in importance. While rays having a wavelength of less than 290 nm (the uvC region) are absorbed by the ozone layer in the earth's atmosphere, rays in the range between 290 nm and 320 nm, the UVB region, cause an erythema, simple sunburn or even burns of varying severity on the skin.

A maximum for the erythema activity of sunlight is given as the relatively narrow range around 308 nm.

Numerous compounds are known for protecting against UVB radiation; these are, inter alia, derivatives of 3-benzylidenecamphor, 4-aminobenzoic acid, cinnamic acid, salicylic acid, benzophenone and 2-phenylbenzimidazole.

It is also important to have available filter substances for the range between about 320 nm and about 400 nm, the UVA region, since its rays can cause reactions in cases of light-sensitive skin. It has been proven that UVA radiation leads to damage of the elastic and collagenous fibers of the connective tissue, leading to premature aging of the skin, and that it is to be regarded as a cause of numerous phototoxic and photoallergic reactions. The harmful effect of UVB radiation can be intensified by UVA radiation.

To protect against UVA rays, derivatives of dibenzoylmethane are used, the photostability of which, however, is inadequate (Int. J. Cosm. Science 10, 53 (1988)).

However, UV radiation can also lead to photochemical reactions, in which case the photochemical reaction products then intervene in the skin's metabolism.

Such photochemical reaction products are mainly free-radical compounds, for example hydroxyl radicals. Undefined free-radical photo products formed in the skin itself can also trigger uncontrolled secondary reactions as a result of their high reactivity. However, singlet oxygen, a non-radical excited state of the oxygen molecule, can also arise during UV irradiation, as can short-lived epoxides and many others. Singlet oxygen, for example, differs from normal triplet oxygen (free-radical ground state) by virtue of its increased reactivity. However, activated, reactive (free-radical) triplet states of the oxygen molecule also exist.

Furthermore, UV radiation is a form of ionizing radiation. There is therefore the risk that ionic species will also form during UV exposure, which then for their part are able to intervene oxidatively in the biochemical processes.

One applications-relevant disadvantage of many UV filters is their poor solubility in water and/or in lipids, as a result of which their use, for example in cosmetic formulations, is often restricted.

A further disadvantage associated with the application of some light protection agents is the appearance of skin irritations and allergies resulting from too high a skin permeability.

GB-A-2 303 549 describes a grinding process for the preparation of micronized insoluble organic UV absorbers in the presence of alkyl polyglycosides. The resulting micronizates can be incorporated into cosmetic light protection preparations.

GB-A-2 286 774 likewise describes a grinding process for the micronization of insoluble organic UV absorbers.

It is an object of the present invention to provide UV light protection agent formulations which bring about effective protection for organic material, in particular for human skin and/or human hair, against UV rays, and which can be readily incorporated into aqueous and into lipophilic systems.

We have found that this object is achieved by aqueous dispersions of sparingly water-soluble or water-insoluble organic UV filter substances which comprise at least one sparingly water-soluble or water-insoluble organic UV filter substance as colloidally disperse phase in amorphous or partially amorphous form.

For the purposes of the present invention, the term "aqueous dispersions" means aqueous suspensions and emulsions. Preferred aqueous suspensions which may be mentioned are those in which the dispersed phase comprises at least one sparingly water-soluble or water-insoluble organic UV filter substance as nanoparticulate particles. Moreover, at the forefront of the invention are also the dry powders or emulsions prepared from the above aqueous suspensions, preferably double emulsions, in particular o/w/o emulsions.

In this connection, the term "sparingly water-soluble organic UV filter substances" means those compounds whose water solubility is <5% by weight, preferably <1% by weight, particularly preferably <0.5% by weight, very particularly preferably <0.1% by weight.

The novel light protection agent formulations are notable for the fact that they comprise at least one sparingly water-soluble or water-insoluble organic UV filter substance whose amorphous proportion is in the range greater than 10%, preferably greater than 30%, particularly preferably in the range from 50 to 100%, very particularly preferably in the range from 75 to 99%. The degree of crystallinity of the UV filter substances can be determined here, for example, by X-ray diffraction measurements.

The content of at least one sparingly water-soluble or water-insoluble organic UV filter substance in the light protection agent formulations according to the invention is in the range from 0.1 to 70% by weight, preferably in the range from 2 to 40% by weight, particularly preferably in the range from 3 to 30% by weight, very particularly preferably in the range from 5 to 25% by weight, based on the dry mass of the formulations.

The mean particle size of the nanoparticulate particles in the aqueous dispersion is, depending on the type of formulation method, in the range below 10 $\mu$m, preferably in the range below 5 $\mu$m, particularly preferably in the range from 0.01 to 2 $\mu$m, very particularly preferably in the range from 0.05 to 1 $\mu$m.

A preferred form of the aqueous dispersions according to the invention is notable for the fact that the particles of the colloidally disperse phase have a core/shell structure, where the core comprises at least one sparingly water-soluble or water-insoluble organic UV filter substance. The shell surrounding the core essentially comprises at least one protective colloid, preferably a relatively high molecular weight compound.

The purpose of this polymer shell is to stabilize the particles in their colloidal state from heterogeneous particle growth (aggregation, flocculation etc.).

One or more polymers can be used for this purpose. The molar masses of the polymers used are in the range from 1000 to 10,000,000 g/mol, preferably in the range from 1000 to 1,000,000 g/mol. In principle, suitable polymers are all those suitable for the pharmaceuticals and cosmetics application sector.

According to the invention, suitable polymeric stabilizers for the coating matrix of the shell are advantageously water-soluble or water-swellable protective colloids such as, for example, cow, pig or fish gelatins, in particular acid- or base-degraded gelatins having Bloom numbers in the range from 0 to 250, very particularly preferably gelatins A 100, A 200, B 100 and B 200, and low molecular weight enzymatically degraded gelatin types having the Bloom number 0 and molecular weights from 15,000 to 25,000 D, such as, for example, Collagel A and Gelitasol P (Stoess, Eberbach), and mixtures of these types of gelatin, and also starch, dextrin, pectin, gum arabic, lignosulfonates, chitosan, polystyrenesulfonate, alginates, caseine, caseinate, methylcellulose, carboxymethylcellulose, hydroxypropylcellulose, milk powder, dextran, full-fat milk or reduced-fat milk or mixtures of these protective colloids. Also suitable are homo- and copolymers based on neutral, cationic or anionic monomers, such as, for example, ethylene oxide, propylene oxide, acrylic acid, maleic anhydride, lactic acid, N-vinylpyrrolidone, vinyl acetate, α- and β-aspartic acid.

The water solubility or water swellability of the abovementioned polymers is dependent on the temperature, the pH and on the ionic strength of the solution.

A further likewise preferred form of the aqueous dispersion according to the invention is notable for the fact that the particles of the colloidally disperse phase additionally comprise a water-insoluble polymer matrix into which at least one sparingly water-soluble or water-insoluble organic UV filter substance has been embedded. To improve the colloidal stability of this aqueous dispersion, it may be advantageous if the dispersed particles have likewise been coated by one of the abovementioned protective colloids.

The matrix polymers on the inside of the particles contribute to keeping the active ingredient in its noncrystalline state, and to stabilizing the colloidal structures with regard to homogeneous particle growth (Ostwald ripening).

Suitable polymeric constituents which are found in the core of the particles of the active ingredient preparation according to the invention are, in principle, all polymers which, in a temperature range between 0 and 240° C., a pressure range between 1 and 100 bar, a pH range from 0 to 14 or ionic strengths up to 10 mol/l, are insoluble or only partially soluble in water or aqueous solutions or water/solvent mixtures.

In this connection, insoluble or only partially soluble means that the $2^{nd}$ virial coefficient for the polymer or polymers in water or a mixture of water and an organic solvent can assume values of less than zero (cf. M. D. Lechner, "Makromolekulare Chemie" [Macromolecular Chemistry], Birkhauser Verlag, Basel, pp. 170–175). The $_2$nd virial coefficient, which gives information about the behavior of a polymer in a solvent (mixture), can be determined experimentally, for example by light-scattering measurement or determination of the osmotic pressure. The dimension of this coefficient is $(mol \cdot l)/g^2$.

It is possible to use one or more polymers. The molar masses of the polymers used are in the range from 1000 to 10,000,000 g/mol, preferably in the range from 1000 to 1,000,000 g/mol. In principle, suitable polymers are all those suitable for the pharmaceuticals and cosmetics application sectors.

Of particular interest are polymers which are soluble in organic water-miscible solvents, and, at temperatures between 0 and 240° C., are insoluble or only partially soluble in water or aqueous solutions or water/solvent mixtures. The following polymers are given by way of example, without, however, imposing any limitation: poly(vinyl ethers), such as, for example, poly(benzyloxyethylene), poly(vinyl acetals), poly(vinyl ketones), poly(allyl alcohol), poly(vinyl esters) such as, for example, poly(vinyl acetate), poly(oxytetramethylene), poly(glutaraldehyde), poly(carbonates), poly(esters), poly(siloxanes), poly(amides), poly(piperazines), poly(anhydrides) such as, for example, poly(metharyl anhydride), gutta percha, cellulose ethers such as, for example, methylcellulose (degree of substitution: 3 to 10%), ethylcellulose, butylcellulose, cellulose esters such as, for example, cellulose acetate or starches. In particular, copolymers and block copolymers of the monomers of the abovementioned polymers. Also copolymers and block copolymers of polyesters and hydroxycarboxylic acids and a linear and star polyethylene glycol, e.g. AB, ABA and ABC block copolymers of a combination of L-poly(lactide), polyglycolide and/or polyethylene glycol, e.g Resomer 505, Resomer RG-756 or Resomer RG-858 (Böhringer Ingelheim).

Of particular interest are also polymers which, at temperatures between 0 and 240° C., have an upper and/or lower miscibility gap in water or aqueous solutions or water/solvent mixtures, i.e. by increasing or lowering the temperature, it is possible to precipitate out these polymers from corresponding solutions. The following polymers are given by way of example, but, however, do not impose any limitation:
poly(acrylamides), poly(methacrylamides) such as, for example, poly(N-isopropylacrylamide), poly(N,N-dimethylacrylamide), poly(N-(1,1-dimethyl-3-oxobutyl) acrylamide), poly(methoxyethylene), poly(vinyl alcohols), acetylated poly(vinyl alcohols), poly(oxyethylene), cellulose ethers such as, for example, methylcellulose (degree of substitution: 20 to 40%), isopropylcellulose, cellulose ester, starches, modified starches such as, for example, methyl ether starch, gum arabic, and copolymers or block copolymers of monomers of the abovementioned compounds. In particular, AB or ABA block copolymers based on ethylene oxide and propylene oxide, e.g. poloxamers, such as poloxamer 188 and poloxamer 407.

Of particular interest are also polymers which, at temperatures between 0 and 240° C., can be precipitated out of corresponding solutions in water or aqueous solutions or water/solvent mixtures by varying the pH or the ionic strength. The following polymers are given by way of example, but do not impose any limitation:
alginates, chitosan, chitin, shellac, polyelectrolytes, poly(acrylic acid), poly(methacrylic acid), poly(methacrylic esters) having secondary tertiary or quaternary amino groups, in particular copolymers or block copolymers based on various acrylates, methacrylates, methacrylic acid, acrylic acid, e.g. a copolymer of methacrylic acid/methacrylic ester (MAA/MAE weight ratio 1:1 or 1:2) or a copolymer of dimethylaminoethyl methacrylate and methacrylic ester in the weight ratio 1:1 (Eudragit$^R$ grades).

The amounts of the various components are chosen according to the invention such that the preparations comprise, in addition to the abovementioned UV filter substances, 0.1 to 80% by weight, preferably 5 to 70% by weight, particularly preferably 10 to 60% by weight, very particularly preferably 15 to 35% by weight, of one or more polymeric protective colloids (coating polymer) and optionally 0.1 to 80% by weight, preferably 0.5 to 70% by weight, particularly preferably 1 to 50% by weight, very particularly preferably 5 to 35% by weight of one or more matrix polymers for the core. The percentages by weight are based on the dry mass of the light protection agent formulation.

In addition, the preparations can also comprise low molecular weight stabilizers, such as antioxidants and/or preservatives for protection of the UV filter substances. Suitable antioxidants or preservatives are, for example, α-tocopherol, ascorbic acid, tert-butylhydroxytoluene, tert-butylhydroxyanisole, lecithin, ethoxyquin, methylparaben, propylparaben, sorbic acid or sodium benzoate. The antioxidants or preservatives can be present in amounts of from 0.01 to 50% by weight, preferably 0.1 to 30% by weight, particularly preferably 0.5 to 20% by weight, very particularly preferably 1 to 10% by weight, based on the dry mass of the light protection agent formulation.

The dispersions can further comprise softeners for increasing the mechanical stability of a dry powder optionally prepared therefrom. Suitable softeners are, for example, sugars and sugar alcohols, such as sucrose, glucose, lactose, inverted sugar, sorbitol, mannitol, xylitol or glycerol. Preference is given to using lactose as softener. The softeners can be present in amounts of from 0.1 to 70% by weight, preferably 10 to 60% by weight, particularly preferably 20 to 50% by weight, based on the dry mass of the light protection agent formulation.

The light protection agent formulations can further comprise low molecular weight surface-active compounds (emulsifiers) in a concentration of from 0.01 to 70% by weight, preferably 0.1 to 50% by weight, particularly preferably 0.5 to 20% by weight, based on the dry mass of the light protection agent formulation. Suitable such compounds are primarily amphiphilic compounds or mixtures of such compounds. In principle, all surfactants with an HLB value of from 5 to 20 are suitable. Suitable corresponding surface-active substances are, for example: esters of long-chain fatty acids with ascorbic acid, mono- and diglycerides of fatty acids and the oxyethylation products thereof, esters of monofatty acid glycerides with acetic acid, citric acid, lactic acid or diacetyltartaric acid, polyglycerol fatty acid esters, such as, for example, the monostearate of triglycerol, sorbitan fatty acid esters, propylene glycol fatty acid esters, and lecithin. Preference is given to using ascorbyl palmitate.

In some instances it may also be advantageous to additionally use a physiologically approved oil, such as, for example, sesame oil, wheatgerm oil, cottonseed oil, soybean oil or groundnut oil, and cosmetic oils, for example paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanolin and stearic acid in a concentration of from 0.1 to 500% by weight, preferably 10 to 300% by weight, particularly preferably 20 to 100% by weight, based on the sparingly water-soluble or water-insoluble organic UV filter substance(s) used.

Sparingly water-soluble or water-insoluble organic UV filter substances which may be used include compounds from the group of triazines, anilides, benzophenones, triazoles, cinnamides and sulfonated benzimidazoles.

The particular embodiment of the aqueous dispersion according to the invention which is to be mentioned are formulations which comprise at least one 1,3,5-triazine derivative of the formula I

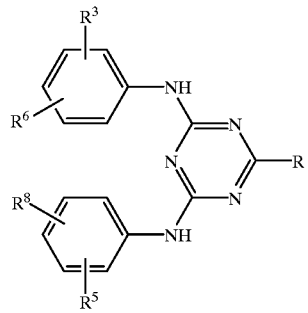

in which the substituents independently of one another have the following meanings:

R
is hydrogen, halogen, OH, $C_1$–$C_{20}$-alkyl, $C_1$–$C_{20}$-alkoxy, $C_1$–$C_{20}$-alkoxyalkyl, $C_1$–$C_{20}$-hydroxyalkoxy, $NR^1R^2$, or a radical of the formula Ia

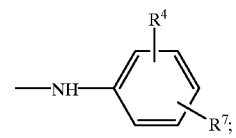

$R^1$ and $R^2$
are hydrogen, $C_1$–$C_{20}$-alkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl;

$R^3$ to $R^5$
are hydrogen, OH, $NR^9R^{10}$, $C_1$–$C_{20}$-alkoxy, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_{5-6}8$-cycloalkyl;

$R^6$ to $R^8$
are hydrogen, $C_1$–$C_{20}$-alkoxy, —C(=O)—$R^{11}$, —C(=O)—X—$R^{12}$, $SO_2R^{13}$, CN;

$R^9$ to $R^{11}$
are hydrogen, $C_1$–$C_{20}$-alkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl;

$R^{12}$ is hydrogen, $C_1$–$C_{20}$-alkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl or a radical of the formula Sp-Sil;

$R^{13}$ is $C_1$–$C_{20}$-alkyl, $C_5$–$C_8$-cycloalkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl;

X is O, NR$^{14}$;

R$^{14}$ is hydrogen, C$_1$–C$_{20}$-alkyl, C$_6$–C$_{12}$-aryl optionally substituted by one or more C$_1$–C$_4$-alkyl, C$_7$–C$_{10}$-aralkyl optionally substituted by one or more C$_1$–C$_4$-alkyl, heteroaryl optionally substituted by one or more C$_1$–C$_4$-alkyl, C$_5$–C$_8$-cycloalkyl;

Sp is a spacer;

Sil is a radical from the group consisting of silanes, oligosiloxanes and polysiloxanes.

Alkyl radicals R, R$^1$ and R$^2$, and R$^9$ to R$^{14}$ which may be mentioned are branched or unbranched C$_1$–C$_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, 1,1,3-trimethylhexyl, 1,1,3,3-tetramethylpentyl, n-nonyl, n-decyl, n-undecyl, 1-methylundecyl, n-dodecyl, 1,1,3,3,5,5-hexamethylhexyl, n-tridecyl, n-tetradecyl, n-pentadecyl, n-hexadecyl, n-heptadecyl, n-octadecyl, n-nonadecyl or n-eicosyl.

Halogen R is fluorine, bromine, iodine or, preferably, chlorine.

Suitable alkoxy radicals R and R$^3$ to R$^8$ are straight-chain and branched radicals having 1 to 20 carbon atoms, preferably having 1 to 12 carbon atoms, particularly preferably having 1 to 8 carbon atoms.

Examples which can be mentioned are:
methoxy
isopropoxy
1-methylpropoxy
n-pentoxy
3-methylbutoxy
2,2-dimethylpropoxy
1-methyl-1-ethylpropoxy-octoxy
ethoxy
n-propoxy
n-butoxy
2-methylpropoxy
1,1-dimethylpropoxy
hexoxy
heptoxy
2-ethylhexoxy Suitable hydroxyalkoxy radicals R are the abovementioned alkoxy radicals having an additional terminal hydroxyl function.

Cycloalkyl radicals R$^1$ to R$^5$ and R$^9$ to R$^{14}$ which may be mentioned are, preferably, branched or unbranched C$_3$–C$_{10}$-cycloalkyl radicals, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. Preference is given to C$_5$–C$_8$-cycloalkyl, such as cyclopentyl, cycloheptyl, cyclooctyl and, in particular, cyclohexyl.

The cycloalkyl radicals can optionally be substituted by one or more, e.g. 1 to 3, radicals such as halogen, e.g. fluorine, chlorine or bromine, cyano, nitrogen, amino, C$_1$–C$_4$-alkylamino, C$_1$–C$_4$-dialkylamino, hydroxyl, C$_1$–C$_4$-alkyl, C$_1$–C$_4$-alkoxy or other radicals, or can comprise 1 to 3 heteroatoms, such as sulfur, nitrogen, whose free valences can be saturated by hydrogen or C$_1$–C$_4$-alkyl, or oxygen in the ring.

Examples of C$_6$–C$_{12}$-aryl which can be mentioned are, in particular, phenyl, naphthyl and biphenyl.

Examples of C$_7$–C$_{10}$-aralkyl are benzyl, phenylethyl, α-methylphenylethyl or α,α-dimethylbenzyl.

Heteroaryl radicals are advantageously single or fused aromatic ring systems having one or more heteroaromatic 3- to 7-membered rings. Heteroatoms which may be present in the ring or ring system are one or more nitrogen, sulfur and/or oxygen atoms.

Suitable substituents of the abovementioned aryl, aralkyl and heteroaryl radicals are C$_1$–C$_4$-alkyl groups, for example methyl, ethyl, n-propyl, 1-methylethyl, n-butyl, 1-methylpropyl, 2-methylpropyl, 1,1-dimethylethyl.

The term spacer for Sp is in this connection a bivalent branched or unbranched C$_3$–C$_{12}$-alkylene or alkenylene chain, which links the silane, oligosiloxane or polysiloxane moiety with the triazine radical.

Examples of a C$_3$–C$_{12}$-alkylene chain are propylene, 2-methylpropylene, butylene, pentylene and hexylene.

Examples of a C$_3$–C$_{12}$-alkenylene chain are 2-propen-2-ylene, 2-methyl-3-propenylene, 3-buten-3-ylene and 4-penten-4-ylene.

Preferred spacers are —(CH$_2$)$_3$—, —(CH$_2$)$_4$—, —(CH$_2$)$_5$—, —[CH(CH$_3$)]—(CH$_2$)—, —(CH$_2$)$_2$—CH=CH—, —C(=CH$_2$)—CH$_2$—, —C(=CH$_2$)—(CH$_2$)$_2$—(CH$_2$)$_4$—, —(CH$_2$)$_4$—(CH$_2$)$_2$—.

The term silanes in this connection stands for a radical SiR$^{15}$R$^{16}$R$^{17}$, in which R$^{15}$, R$^{16}$, R$^{17}$, independently of one another, are C$_1$–C$_6$-alkyl, C$_1$–C$_6$-alkoxy or phenyl.

Examples which may be mentioned are: Si(CH$_2$—CH$_3$)$_3$, Si(CH$_2$—CH$_2$—CH$_3$)$_3$, Si(isopropyl)$_3$, Si(tert-butyl)$_3$, Si(tert-butyl)(CH$_3$)$_2$, Si(CH$_3$)$_2$ (hexyl), Si(OCH$_3$)$_3$, Si(OEt)$_3$, SiPh$_3$.

The term oligosiloxanes means a radical from the group of the formula consisting of SiR$^{18}$$_m$(OSiR$^{18}$$_3$)$_n$ where m=0, 1 or 2; n=3, 2 or 1 and m+n=3, R$^{18}$—[Si(R$^{18}$)$_2$—O—]$_r$—Si(R$^{18}$)$_2$—A and R$^{18}$—[Si(R$^{18}$)$_2$—O—]$_r$—Si(A)(R$^{18}$)—O—Si(R$^{18}$)$_3$, in which A is a chemical bond or a spacer and R$^{18}$ is a C$_1$–C$_6$-alkyl radical or phenyl radical, and r is a value from 1 to 9.

The term polysiloxanes includes, for example, a radical from the group of the formula consisting of A—[Si(R$^{19}$)$_2$—O]$_s$—Si(R$^{19}$)$_2$—A or (R$^{19}$)$_3$—Si—[O—Si(R$^{19}$)$_2$]$_t$—[O—Si(R$^{19}$)(A)]$_q$—O—Si(R$^{19}$)$_3$, in which A is a chemical bond or a spacer, and R$^{19}$ is a C$_1$–C$_6$-alkyl radical or phenyl radical, s and t are values from 4 to 250, and q is a value from 1 to 30.

Examples of silanyl-triazines in which R$^{12}$ is a radical of the formula Sp-Sil are given in EP-A-0 933 376.

At the forefront of interest are triazine compounds of the formula Ib,

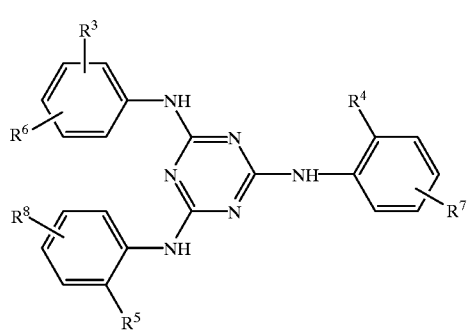

Ib in which R$^3$ to R$^5$ are in the ortho-position relative to the phenylamino radical of the triazine.

Preference is given to an aqueous dispersion comprising at least one 1,3,5-triazine derivative of the formula Ib in which the substituents, independently of one another, have the following meanings:

$R^3$ to $R^5$ are hydrogen, OH;

$R^6$ to $R^8$ are $C_1$-$C_{12}$-alkoxy, —C(=O)—X—$R^{12}$;

X is O, $NR^{14}$;

$R^{12}$ and $R^{14}$ are hydrogen, $C_4$-$C_8$-alkyl.

A particularly advantageous UVB filter is 2,4,6-trianilino-p-(carbo-2'-ethylhexyl-1'-oxy)-1,3,5-triazine, which is marketed by BASF Aktiengesellschaft under the trade name Uvinul® T150.

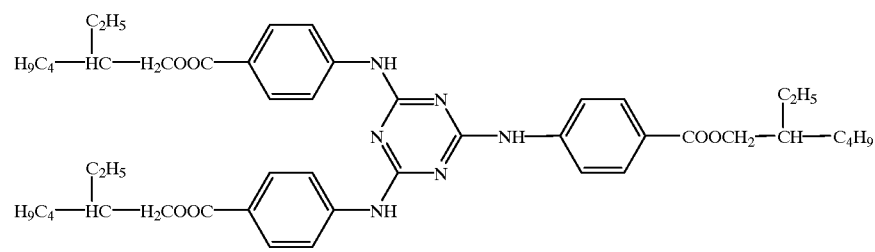

Uvinul® T150 is notable for good UV absorption properties and an extremely high absorbance coefficient of >1500 and 314 nm.

Other sparingly water-soluble or water-insoluble organic UV filter substances from the group of triazines which may be mentioned are, inter alia, the following compounds described in WO 94/05645 and EP-A-0 444 323:

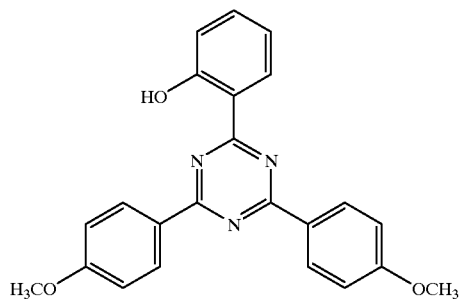

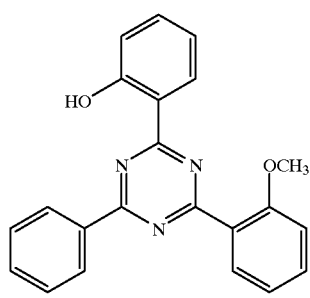

-continued

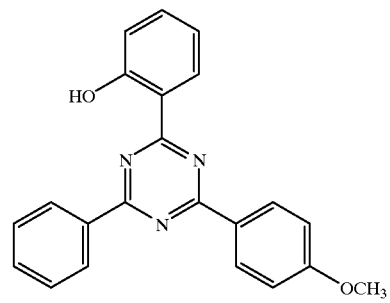

-continued

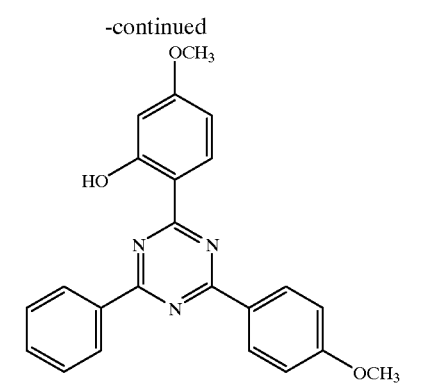

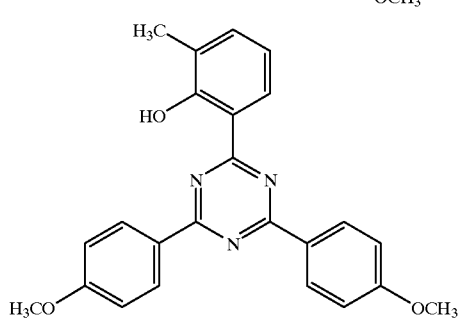

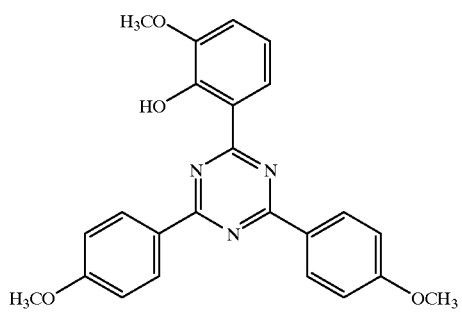

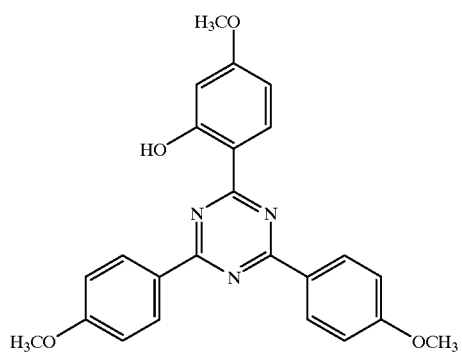
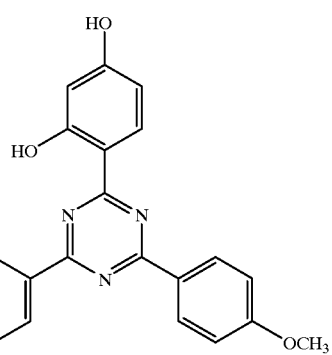
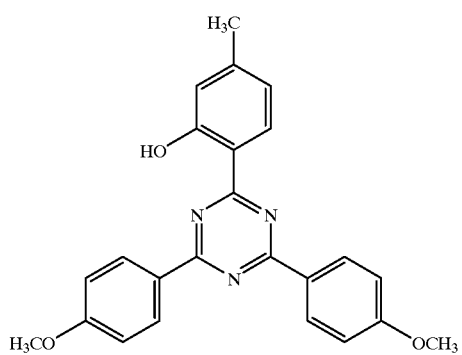
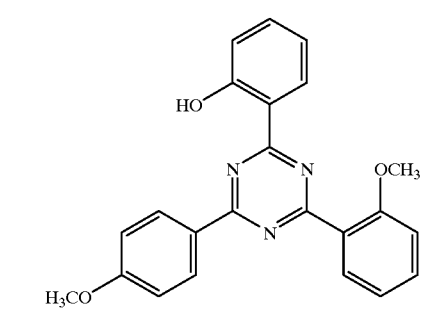
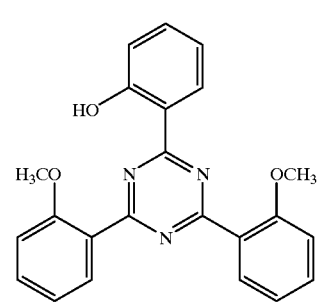
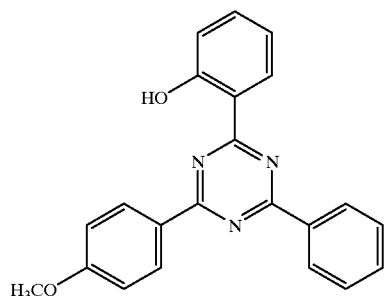
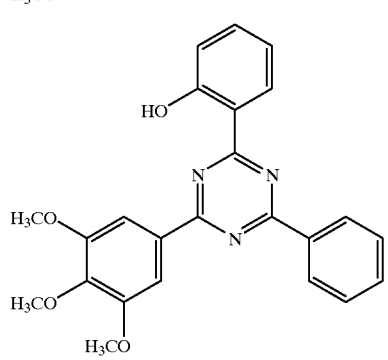
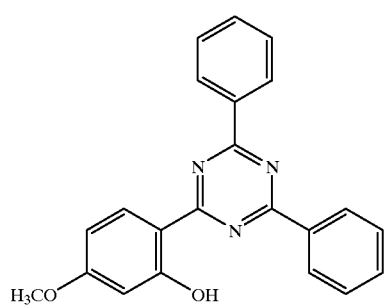
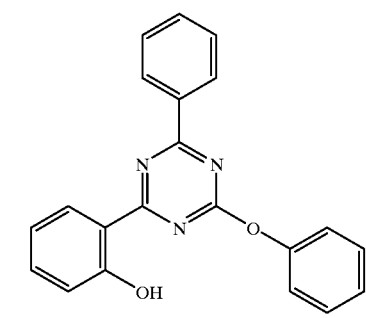
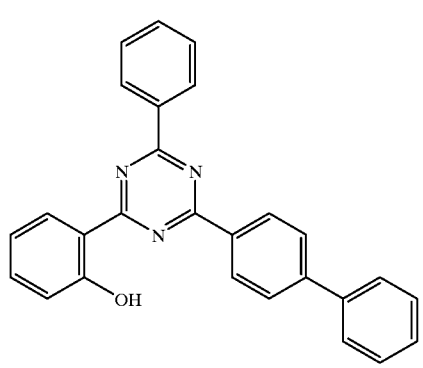

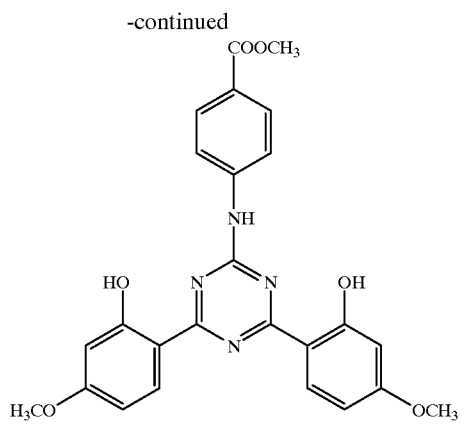

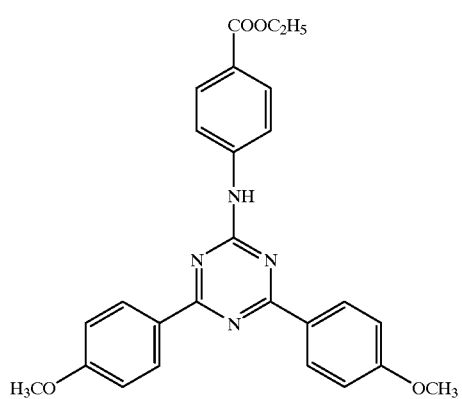

Preferred anilides are compounds of the formula II, in which $W^1$ and $W^2$, independently of one another, are $C_1$–$C_{18}$-alkyl or $C_1$–$C_{18}$-alkoxy.

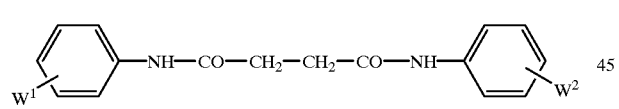

Particular preference is given to N-(2-ethoxyphenyl)-N'-(2-ethylphenyl)ethanediamide.

Preferred triazoles are compounds of the formula III in which, independently of one another, $T^1$ is $C_1$–$C_{18}$-alkyl or hydrogen, and $T^2$ and $T^3$ are $C_1C_{18}$-alkyl.

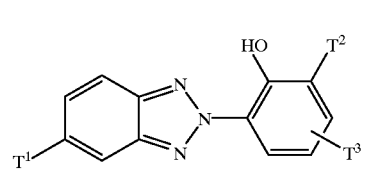

A further preferred class of compound of water-insoluble triazoles are compounds of the formula IIIa, in which $T^4$ and $T^5$ independently of one another are $C_1$–$C_{18}$-alkyl.

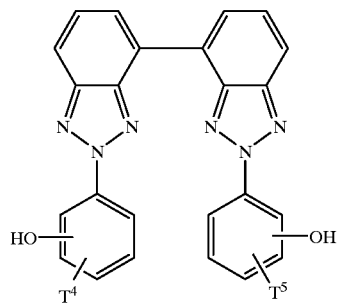

Likewise preferred representatives from the group of water-insoluble triazoles are compounds of the formulae IIIb and IIIc, in which $T^6$ and $T^7$ independently of one another are $C_1$–$C_{18}$-alkyl, preferably tert-butyl, —C(CH$_3$)$_2$—CH$_2$—C(CH$_3$)$_3$ or 2-ethylhexyl. Both radicals $T^6$ and $T^7$ are —C(CH$_3$)$_2$—CH$_2$—C(CH$_3$)$_3$ in the particularly preferred compound of the formula IIIb. $T^8$ in the formula IIIc is likewise $C_1$–$C_{18}$-alkyl, preferably methyl.

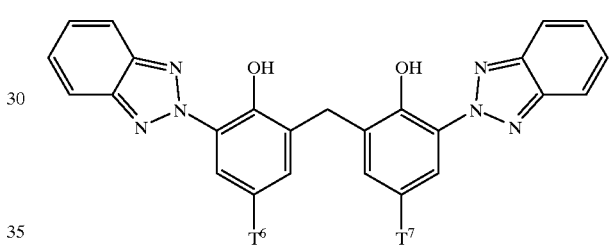

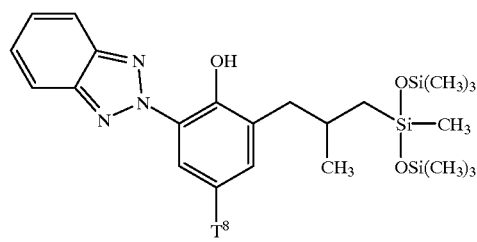

Preferred cinnamides are compounds of the formula IV, in which, independently of one another, $Y^1$ and $Y^2$ are hydrogen or $C_1$–$C_4$-alkyl, preferably methyl or ethyl, and $Y^3$ is aryl, preferably phenyl or 4-methoxyphenyl.

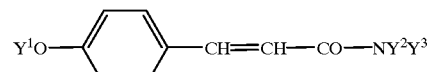

Preferred sulfonated benzimidazoles are compounds of the formula V, in which M is hydrogen, an alkali metal—preferably sodium—or an alkaline earth metal such as magnesium, calcium or zinc.

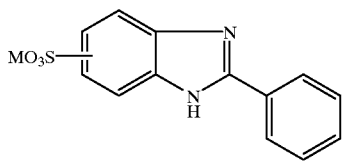

Preferred benzophenones are compounds of the formula VI, in which, independently of one another, $M^1$ to $M^4$ are hydrogen or $C_1$–$C_4$-alkyl, $M^1$ and $M^4$ are preferably methyl or ethyl, and $M^2$ and $M^3$ are preferably hydrogen.

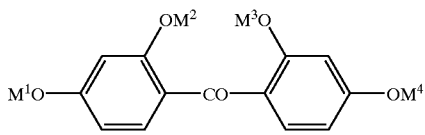

The spherical isotropic character of the particles present in the dispersions according to the invention does not exhbit pseudoplastic behavior, in contrast to ground anisotropic particles. Incorporation of this dispersion, for example into cosmetic formulations, and the use of these formulations is therefore significantly easier.

In addition, we have found that a sunscreen cream based on the dispersion according to the invention has a sun protection factor which is higher by a factor of 4 than an analogous light protection agent preparation in which the same amount of UV filter substance was present in molecularly disperse form.

While ground UV filter substances have an increased tendency toward particle size growth upon incorporation into skin cream, which can lead to an impairment of the sunscreen factor and to an unpleasant feel on the skin, the dispersons according to the invention do not exhibit such tendencies because of their matrix and protective colloid structure.

The invention also relates to a process for the preparation of an aqueous dispersion comprising at least one sparingly water-soluble or water-insoluble organic UV filter substance as colloidally disperse phase in amorphous or partially amorphous form, which comprises
a) preparing a molecularly disperse solution of at least one sparingly water-soluble or water-insoluble organic UV filter substance in an organic solvent,
b) treating this solution with an aqueous solution of at least one protective colloid, the hydrophobic phase of the UV filter substance forming as colloidally disperse phase, and
c) freeing the resulting dispersion from the organic solvent.

The organic solvent used in process step a) is advantageously at least one water-miscible organic solvent or a mixture of water and at least one water-miscible organic solvent.

Preferred solvents which can be mentioned are primarily those water-miscible, thermally stable, volatile solvents containing only carbon, hydrogen and oxygen, such as alcohols, ethers, esters, ketones and acetals. Expediently, use is made of solvents which are at least 10% water-miscible, have a boiling point below 200° C. and/or have fewer than 10 carbon atoms. Particular preference is given to ethanol, n-propanol, isopropanol, 1,2-butanediol 1-methyl ether, 1,2-propanediol 1-n-propyl ether, tetrahydrofuran or acetone.

The process is further notable for the fact that further additives chosen from the group consisting of emulsifiers, antioxidants, preservatives, water-insoluble polymers and edible oils are optionally added to the solution in step a), and/or that, in step b), the aqueous protective colloid solution additionally comprises at least one softener. It is, however, also possible to add one or more emulsifiers to the protective colloid solution. For a description of these additives, reference may be made to the explanations already given in the introduction.

In a preferred variant of the process, in step a), the molecularly disperse solution of at least one sparingly water-soluble or water-insoluble organic UV filter substance is prepared at-temperatures greater than 15° C., preferably at temperatures in the range from 50° C. to 240° C., particularly preferably in the range from 140° C. to 180° C., and, immediately thereafter, is treated, in step b), with the aqueous solution of the protective colloid, a mixing temperature of from about 35° C. to 120° C., particularly preferably from 55° C. to 70° C., being established.

The invention further relates to a process for the preparation of an aqueous dispersion of at least one sparingly water-soluble or water-insoluble organic UV filter substance, in which the particles of the colloidally disperse phase comprise a water-insoluble polymer matrix into which at least one sparingly water-soluble or water-insoluble organic UV filter substance has been embedded, which comprises
a) preparing a molecularly disperse solution of at least one sparingly water-soluble or water-insoluble organic UV filter substance and a water-insoluble polymer in an organic solvent,
b) treating this solution with water or an aqueous solution of at least one protective colloid, the hydrophobic phase of the mixture comprising UV filter substance and water-insoluble polymer forming as colloidally disperse phase, and
c) freeing the resulting dispersion from the organic solvent.

According to one variant of the process, a molecularly disperse solution of the UV filter substance in the chosen solvent together with the polymer which is to be present in the core of the particles in the light protection agent preparation is prepared. This polymer has the property of being insoluble or only partially soluble in water in a certain temperature, pH or salt range.

The concentration of the resulting light protection agent polymer solution is generally 10 to 500 g of at least one sparingly water-soluble or water-insoluble UV filter substance per 1 kg of solvent and 0.01 to 400 g of polymer, where the polymer : light protection agent weight ratio is between 0.01:1 and 5:1. In a preferred version of the process, the low molecular weight stabilizer is added directly to the light protection agent polymer solution.

In a subsequent process step, the light protection agent polymer solution is mixed with water or, preferably, an aqueous solution of the polymeric coating material. The concentration of the polymeric coating material is generally 0.1 to 200 g/l, preferably 1 to 100 g/l.

According to a further variant of the process, a molecularly disperse solution of the UV filter substance in the chosen solvent without the polymer which is to be present in the core of the particles in the light protection agent preparation is prepared. The concentration of the resulting light protection agent solution is generally 10 to 500 g of UV filter substance per 1 kg of solvent.

In a subsequent process step, this solution is mixed with an aqueous molecular solution of the polymer which is to be present in the core of the particles in the light protection agent preparation. The concentration of the resulting polymer solution is generally 0.01 to 400 g of polymer. Here, the temperatures, pH and salt concentrations of the two solutions to be combined are chosen such that, following combination of the solutions, the UV filter substance and the polymer are insoluble in the combined solution. In a preferred variant of the process, the low molecular weight stabilizer is added directly to the active ingredient solution.

In a subsequent process step, the light protection agent polymer precipitate is mixed with an aqueous solution of the polymeric coating material. The concentration of the polymeric coating material is 0.1 to 200 g/l, preferably 1 to 100 g/l.

The mixing operation can be carried out batchwise or, preferably, continuously. The result of the mixing operation is precipitation.

Which conditions are to be chosen during implementation of the process according to the invention with regard to the variation of the water/organic solvent system, the pH values, the temperatures or the ionic strength in a specific case can be determined for the corresponding polymer by a person skilled in the art using the $2^{nd}$ virial coefficient by a few simple preliminary experiments.

The invention also relates to a process for the preparation of a dry powder comprising at least one sparingly water-soluble or water-insoluble organic UV filter substance as nanoparticulate particles in amorphous or partially amorphous form, which comprises freeing one of the abovementioned aqueous dispersions according to the invention from water, and drying it, optionally in the presence of a coating material.

Conversion into a dry powder can, for example, take place by spray drying, freeze drying or drying in a fluidized bed, optionally also in the presence of a coating material. Suitable coating agents are inter alia corn starch, silica and also tricalcium phosphate.

During the lyophilization of the nanoparticles according to the invention, cryoprotective substances, such as, for example, trehalose or polyvinylpyrrolidones, can be added.

According to the invention, dry powders can thus be obtained which no longer lose their properties obtained in the primary dispersion. This means that the amorphous character of the UV filter substance and the core-shell structure is retained. It is a further property according to the invention that, upon renewed dissolution these dispersions exhibit the same particle size distribution with a deviation of 20%, preferably <15%, as they had as a primary dispersion.

Claimed are also pulverulent preparations obtainable by one of the abovementioned processes, comprising at least one sparingly water-soluble or water-insoluble organic UV filter substance as nanoparticulate particles in amorphous or partially amorphous form.

The invention likewise relates to a process for the preparation of an oil-miscible preparation in the form of a double dispersion, comprising at least one sparingly water-soluble or water-insoluble organic UV filter substance in amorphous or partially amorphous form, which comprises emulsifying the aqueous dispersions described at the outset in oil.

In this connection, by using an emulsifier, a water-in-oil emulsion forms in which the water phase comprises protective-colloid-stabilized nanoparticles of at least one sparingly water-soluble or water-insoluble organic UV filter substance. Suitable emulsifiers are W/O emulsifiers known per se and having an HLB value of less than 10, in particular of 2 to 6 (cf. H. P. Fiedler, Lexikon der Hilfsstoffe für Pharmazie, Kosmetik und angrenzende Gebiete [Lexicon of auxiliaries for pharmacy, cosmetics and related fields], 1996, pages 753 et seq.). Typical representatives of this class of emulsifiers are partial fatty acid esters of polyhydric alcohols, e.g. glycerol monostearate or mixtures of mono-, di- and triglycerides, partial fatty acid esters of sorbitan and/or, preferably, fatty acid esters of polyglycerol, such as, for example, polyglycerol polyricinoleate, which are used in a concentration of from 10 to 1000% by weight, preferably 100 to 900% by weight, particularly preferably 400 to 800% by weight, based on the UV filter substance(s).

The dispersant can be either synthetic, mineral, vegetable or animal in origin. Typical representatives are inter alia sesame oil, corn oil, cottonseed oil, soybean oil or peanut oil, esters of medium-chain vegetable fatty acids, and paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanolin and stearic acid. The amount of dispersant is generally 30 to 95% by weight, preferably 50 to 80% by weight, based on the total mass of the finished emulsion.

The emulsification can be carried out continuously or batchwise.

The physical stability of the double dispersion system, such as, for example, the sedimentation stability, is achieved by very good fine distribution of the water phase in the oil phase, e.g. by intensive treatment with a rotor/stator disperser at temperatures of from 20 to 80° C., preferably 40 to 70° C. or using a high-pressure homogenizer, such as an APV Gaulin or using a very high-pressure homogenizer, such as Microfluidizer, in the pressure range from 700 to 1000 bar. The mean diameters of the aqueous-disperse phase achievable therewith are less than 500 $\mu$m, preferably less than 100 $\mu$m, particularly preferably less than 10 $\mu$m, in particular less than 1 $\mu$m.

The invention also relates to liquid oil-miscible preparations of at least one sparingly water-soluble or water-insoluble organic UV filter substance obtainable by the abovementioned process, which comprise, as double dispersion systems, an aqueous-disperse phase having a particle diameter of less than 500 $\mu$m, in which protective-colloid-stabilized particles of one or more sparingly water-soluble- or water-insoluble organic UV filter substances are present in dispersed form, in an oil as dispersant.

The formulations according to the invention—dispersions and dry powders prepared therefrom—are highly suitable for stabilizing organic material inter alia against the effect of light, oxygen and heat. They are added to the organic material to be stabilized in a concentration of from 0.01 to 10% by weight, preferably 0.01 to 5% by weight, particularly preferably from 0.02 to 2% by weight, based on the organic material, before, during or after its preparation.

The term "organic material" means, for example, photographic recording materials, in particular photographic emulsions or precursors for plastics and surface coatings, in particular, however, plastics and surface coatings themselves.

Organic material, however, also means cosmetic preparations, such as, for example, creams, lotions, gels, lipsticks.

The present invention further relates to organic material stabilized against the action of light, oxygen and heat, in particular plastics and surface coatings, comprising 0.01 to 10% by weight, preferably 0.01 to 5% by weight, particularly preferably from 0.02 to 2% by weight, based on the total amount of the organic material, of one or more sparingly water-soluble or water-insoluble organic UV filter substances in the form of the formulations according to the invention.

For mixing the formulations according to the invention primarily with plastics, it is possible to use all known devices and methods for mixing stabilizing agents or other additives into polymers.

The organic material stabilized by the formulations according to the invention can optionally comprise further additives, e.g. antioxidants, light stabilizing agents, metal deactivators, antistatic agents, flame retardants, pigments and fillers.

Antioxidants and light stabilizers which can be added in addition to the formulations according to the invention are, for example, compounds based on sterically hindered phenols or costabilizers containing sulfur or phosphorus.

Examples of such phenolic antioxidants which may be mentioned are 2,6-di-tert-butyl-4-methylphenol, n-octadecyl-β-(3,5-di-tert-butyl-4-hydroxyphenyl) propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)-benzene, 1,3,5-tris(3,5-di-tert-butyl-4-hydroxybenzyl) isocyanurate, 1,3,5-tris[β-(3,5-di-tert-butyl-4-hydroxyphenyl) propionylethyl] isocyanurate, 1,3,5-tris(2,6-dimethyl-3-hydroxy-4-tert-butylbenzyl) isocyanurate and pentaerythritol tetrakis[β-(3,5-di-tert-butyl-4-hydroxyphenyl) propionate].

Examples of suitable phosphorus-containing antioxidants are tris(nonylphenyl) phosphite, distearylpentaerythritol diphosphite, tris(2,4-di-tert-butylphenyl) phosphite, tris(2-tert-butyl-4-methylphenyl) phosphite, bis(2,4-di-tert-butylphenyl)pentaerythritol diphosphite and tetrakis(2,4-di-tert-butylphenyl) 4,4,-biphenylenediphosphite. Examples of sulfur-containing antioxidants which may be mentioned are dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Other antioxidants and light stabilizers which can be used together with the formulations according to the invention are, for example, 2-(2'-hydroxyphenyl)benzotriazoles, 2-hydroxybenzophenones, aryl esters of hydroxybenzoic acids, α-cyanocinnamic acid derivatives, benzimidazolecarboxanilides, nickel compounds or oxalanilides.

Particularly good stabilization is achieved when at least one light stabilizer from the compound class of sterically hindered amines is also added in the usual concentration to the formulations according to the invention.

Examples of suitable sterically hindered amines are: bis(2,2,6,6-tetramethylpiperidyl) sebacate, bis(1,2,2,6,6-pentamethylpiperidyl) sebacate, the condensation product of 1-hydroxyethyl-2,2,6,6-tetramethyl-4-hydroxypiperidine and succinic acid, the condensation product of N,N'-di(2,2,6,6-tetramethylpiperidyl)hexamethylenediamine and 4-tert-octylamino-2,6-dichloro-1,3,5-triazine, tris(2,2,6,6-tetramethylpiperidyl) nitrilotriacetate, tetrakis(2,2,6,6-tetramethyl-4-piperidyl) 1,2,3,4-butanetetracarboxylate, 1,1-(1,2-ethanediyl)-bis(3,3,5,5-tetramethylpiperazinone), the condensation products of 4-amino-2,2,6,6-tetramethylpiperidines and tetramethylolacetylenediureas.

Examples of plastics which can be stabilized by the compounds I according to the invention which may be mentioned are:

polymers of mono- and diolefins, such as, for example, low density or high density polyethylene, polypropylene, linear poly-1-butene, polyisoprene, polybutadiene, and copolymers of mono- or diolefins or mixtures of said polymers;

copolymers of mono- or diolefins with other vinyl monomers, such as, for example, ethylene/alkyl acrylate copolymers, ethylene/alkyl methacrylate copolymers, ethylene/vinyl acetate copolymers or ethylene/acrylic acid copolymers;

polystyrene and copolymers of styrene or α-methylstyrene with dienes and/or acrylic derivatives, such as, for example, styrene/butadiene, styrene/acrylonitrile (SAN), styrene/ethyl methacrylate, styrene/butadiene/ethyl acrylate, styrene/acrylonitrile/methacrylate, acrylonitrile/butadiene/styrene (ABS) or methyl methacrylate/butadiene/styrene (MBS);

halogen-containing polymers, such as, for example, polyvinyl chloride, polyvinyl fluoride, polyvinylidene fluoride and copolymers thereof;

polymers derived from α,β-unsaturated acids and derivatives thereof, such as polyacrylates, polymethacrylates, polyacrylamides and polyacrylonitriles;

polymers derived from unsaturated alcohols and amines or acyl derivatives or acetals thereof, e.g. polyvinyl alcohol and polyvinyl acetate;

polyurethanes, polyamides, polyureas, polyesters, polycarbonates, polysulfonates, polyether sulfones and polyether ketones.

Furthermore, the formulations according to the invention can be used to stabilize surface coatings, e.g. industrial finishes. Of these, particular attention is drawn to baking finishes, and, in turn, of these, automotive finishes, preferably two-coat finishes.

The formulations can be added in solid or liquid form to the surface coating. Their good solubility in surface coating systems is of particular advantage here.

Even in the case of the use as stabilizers in surface coatings, it is possible also to use the additional additives already listed, in particular antioxidants and light stabilizers.

The formulations according to the invention are notable for good compatibility with the other types of plastics and good solubility in customary surface coating systems and in customary cosmetic oils. They are generally colorless or have only a slight intrinsic color, are stable and nonvolatile at the customary processing temperatures for plastics and surface coatings, show only a slight tendency to migrate and, above all, effect a long period of protection of the organic materials treated therewith.

Furthermore, the light protection agent formulations according to the invention are also suitable as photostable UV filters in cosmetic and pharmaceutical preparations for protecting human skin or human hair from solar rays and also from artificial light which has high UV contents, alone or together with compounds which absorb in the UV region and are known for cosmetic or pharmaceutical preparations. Thus, in the widest sense, the term organic materials also means human skin and human hair. The cosmetic and pharmaceutical preparations as such are of course also stabilized at the same time in order to remain effective for as long as possible.

Accordingly, the present invention also relates to cosmetic and pharmaceutical preparations comprising light protection agents for protecting human skin or human hair from UV light in the range from 280 to 400 nm, which comprise, as photostable UV filters and in a cosmetically or pharmaceutically suitable carrier, effective amounts of a formulation of sparingly water-soluble or water-insoluble organic UV filter substances in amorphous or partially amorphous form—alone or together with compounds which absorb in the UV-A and UV-B region and are known per se for cosmetic and pharmaceutical preparations—the formulations being aqueous dispersions according to the invention mentioned in the introduction or the o/w/o emulsions or dry powders prepared therefrom.

The amount of sparingly water-soluble or water-insoluble organic UV filter substance in the form of the formulations according to the invention which is used in the cosmetic and pharmaceutical preparations is in the range from 0.05 to 20% by weight, preferably 0.1 to 10% by weight, particularly preferably in the range from 1 to 7% by weight, based on the total amount of the cosmetic and pharmaceutical preparation.

The cosmetic and pharmaceutical preparations comprising light protection agents are generally based on a carrier which comprises at least one oil phase. Preparations based solely on aqueous components are, however, also possible. Accordingly, suitable preparations are oils, oil-in-water and water-in-oil emulsions, creams and pastes, lip-protection stick compositions or grease-free gels.

Suitable emulsions are inter alia also O/W macroemulsions, O/W microemulsions or O/W/O emulsions containing amino-substituted hydroxybenzophenones of the formula I present in dispersed form, the emulsions being obtainable by phase inversion technology, as in DE-A-197 26 121.

Customary cosmetic auxiliaries which may be suitable as additives are, for example, coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators. Suitable coemulsifiers are, preferably, known W/O and also O/W emulsifiers, such as, for example, polyglycerol esters, sorbitan esters or partially esterified glycerides. Typical examples of fats are glycerides; waxes which may be mentioned are inter alia beeswax, paraffin wax or microcrystalline waxes, optionally in combination with hydrophilic waxes. Stabilizers which may be used are metal salts of fatty acids, such as, for example, magnesium, aluminum and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, and also fatty alcohols, monoglycerides and fatty acids, polycrylates, polyvinyl alcohol and polyvinylpyrrolidone. The term biogenic active ingredients means, for example, plant extracts, protein hydrolyzates and vitamin complexes. Customary film formers are, for example, hydrocolloids, such as chitosan, microcrystalline chitosan or polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlizing agents are glycol distearic esters, such as ethylene glycol distearate, but also fatty acids and fatty acid monoglycol esters. Dyes which may be used are the substances suitable and approved for cosmetic purposes, as listed, for example, in the publication "Kosmetische Farbemittel" [Cosmetic Colorants] from the Farbstoffkommission der Deutschen Forschungsgemeinschaft [Dyes Commission of the German Research Council], published by Verlag Chemie, Weinheim, 1984. These dyes are usually used in a concentration of from 0.001 to 0.1% by weight, based on the total mixture.

An additional content of antioxidants is generally preferred. Thus, favorable antioxidants which can be used are all antioxidants which are suitable or customary for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotene (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thiorodoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximines, buthionine sulfones, penta-, hexa-, heptathionine sulfoximine) in very low tolerated doses (e.g. pmol to µmol/kg), also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives thereof (e.g. ascorbyl palmitate, Mg ascorbyl phosphate, ascorbyl acetate), tocopherol and derivatives (e.g. vitamin E acetate, tocotrienol), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide).

The amount of the abovementioned antioxidants (one or more compounds) in the preparations is preferably 0.001 to 30% by weight, particularly preferably 0.05 to 20% by weight, in particular 1 to 10% by weight, based on the total weight of the preparation.

If vitamin E and/or derivatives thereof are the antioxidant or antioxidants, it is advantageous to choose the respective concentrations thereof from the range 0.001 to 10% by weight, based on the total weight of the formulation.

If vitamin A and/or derivatives thereof or carotenoids are the antioxidant or antioxidants, it is advantageous to choose the respective concentration thereof from the range 0.001 to 10% by weight, based on the total weight of the formulation.

Customary oil components in cosmetics are, for example, paraffin oil, glyceryl stearate, isopropyl myristate, diisopropyl adipate, cetylstearyl 2-ethylhexanoate, hydrogenated polyisobutene, vaseline, caprylic/capric triglycerides, microcrystalline wax, lanolin and stearic acid.

The total proportion of auxiliaries and additives can be 1 to 80% by weight, preferably 6 to 40% by weight, and the nonaqueous proportion ("active substance") can be 20 to 80% by weight, preferably 30 to 70% by weight, based on the compositions. The compositions can be prepared in a manner known per se, i.e. for example by hot, cold, hot-hot/cold or PIT emulsification. This is a purely mechanical process, and no chemical reaction takes place.

Such sunscreen preparations can accordingly be in liquid, paste or solid form, for example as water-in-oil creams, oil-in-water creams and lotions, aerosol foam creams, gels, oils, marking pencils, powders, sprays or alcohol-aqueous lotions.

Finally, it is possible additionally to use further substances known per se which absorb in the UV region, provided they are stable in the overall system of the combination of UV filters to be used according to the invention.

The majority of light protection agents in the cosmetic and pharmaceutical preparations used to protect the human epidermis consists of compounds which absorb UV light in the UV-B region, i.e. in the range from 280 to 320 nm. For example, the proportion of the UV-A absorbers to be used according to the invention is 10 to 90% by weight, preferably 20 to 50% by weight, based on the total amount of UV-B and UV-A absorbing substances.

Suitable UV filter substances which are used in combination with the formulations to be used according to the invention are any UV-A and UV-B filter substances. Examples which may be mentioned are:

| No. | Substance | CAS No. (= acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxy-benzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)-bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxy-benzophenone-5-sulfonic acid (sulisobenzone) and the sodium salt | 4065-45-6 |
| 13 | 3-(4'-Sulfobenzylidene)bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Trianiline(o-carbo-2'-ethylhexyl-1'-oxy)-1,3,5-triazine | 88122-99-0 |
| 18 | 3-Imidazol-4-ylacrylic acid and its ethyl ester | 104-98-3 |
| 19 | Ethyl 2-cyano-3,3-diphenylacrylate | 5232-99-5 |
| 20 | 2'-Ethylhexyl 2-cyano-3,3-diphenylacrylate | 6197-30-4 |
| 21 | Menthyl o-aminobenzoate or: 5-methyl-2-(1-methylethyl)-2-aminobenzoate | 134-09-8 |
| 22 | Glyceryl p-aminobenzoate or: 1-glyceryl 4-aminobenzoate | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-1 |
| 27 | 3-(4'Sulfobenzylidene)bornan-2-one and its salt | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |
| 30 | 2,2'-Methylenebis[6(2H-benzotriazol-2-yl)-4-(1,1,3,3-tetramethylbutyl)phenol] | 103597-45-1 |
| 31 | 2,2'-(1,4-Phenylene)-bis-1H-benzimidazole-4,6-disulfonic acid, Na salt | 180898-37-7 |
| 32 | 2,4-bis[4-(2-Ethylhexyloxy)-2-hydroxy]phenyl-6-(4-methoxyphenyl)-(1,3,5)-triazine | 187393-00-6 |
| 33 | 3-(4-Methylbenzylidene)camphor | 36861-47-9 |
| 34 | Polyethoxyethyl 4-bis(polyethoxy)paraaminobenzoate | 113010-52-9 |
| 35 | 2,4-Dihydroxybenzophenone | 131-56-6 |
| 36 | 2,2'-Dihydroxy-4,4'-dimethoxybenzophenone-5,5'-disodium sulfonate | 3121-60-6 |

Polymeric or polymer-bonded filter substances can also be used according to the invention.

The cosmetic and dermatological preparations according to the invention can additionally advantageously comprise inorganic pigments based on metal oxides and/or other metal compounds which are insoluble or sparingly soluble in water, for example the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides. Particular preference is given to pigments based on $TiO_2$ and ZnO.

For the purposes of the present invention, it is particularly advantageous, although not obligatory, for the inorganic pigments to be in hydrophobic form, i.e. to have been surface-treated to repel water. This surface treatment may involve providing the pigments with a thin hydrophobic layer by a method known per se, as described in DE-A-33 14 742.

To protect human hair from UV rays, the light protection agent formulations according to the invention can be incorporated into shampoos, lotions, gels, hairsprays, aerosol foam creams or emulsions in concentrations of from 0.1 to 10% by weight, preferably 1 to 7% by weight. The respective formulations can inter alia be used for washing, coloring and for styling hair.

The formulations to be used according to the invention are usually notable for a particularly high absorbance in the UV-A radiation region with a sharp band structure. Moreover, they are readily soluble in cosmetic oils and can easily be incorporated into cosmetic formulations. The emulsions prepared with the formulations are particularly notable for their high stability, the formulations I themselves are notable for their high photostability, and the preparations prepared therewith are notable for their pleasant feel on the skin.

The UV filter action of the formulations according to the invention can also be utilized for stabilizing active ingredients and auxiliaries in cosmetic and pharmaceutical formulations.

The preparations according to the invention are notable for particularly high absorbance in the UV-B radiation region with a sharp band structure and high light protection factors.

In particular, the high light protection factor of the preparations which was measured even at low concentrations of UV-absorbing active ingredients was surprising.

The examples below serve to illustrate the present invention without limiting it.

EXAMPLE 1

Preparation of a Uvinul® T 150-containing Dry Powder Having an Active Ingredient Content of 20% by Weight a) Preparation of the Aqueous Dispersion 10 g of Uvinul® T 150 were dissolved in 216 g of acetone at room temperature to give a molecularly disperse solution. To precipitate out the Uvinul® T 150 in colloidally disperse form, the solution was passed at 240° C. to a mixing chamber where it was mixed with an aqueous solution, adjusted to pH 9.1 using 1 N NaOH, of 16.88 g of gelatin B 100 Bloom and 11.25 g of lactose in 1500 ml of demineralized water. The entire process was carried out with a pressure limit of 40 bar in order to prevent evaporation of the solvent. After mixing, a colloidally disperse Uvinul® T 150 dispersion with a white cloudy hue was obtained.

Fraunhofer diffraction was used to determine the mean volume distribution to be D (4.3)=0.50 μm with a fines content of the distribution of 98.5% <1.22 μm.

b) Preparation of a Uvinal® T150-containing Aqueous Dry Powder

Spray-drying of the dispersion resulted in a dry powder having an active ingredient content of 20.56% by weight of Uvinul® T 150 (content determination by means of UV/VIS spectroscopy). The dry powder could be redispersed in demineralized water again to form a white cloudy dispersion (hydrosol).

Fraunhofer diffraction was used to determine the mean volume distribution in the redispersion to be D (4.3)=0.65 μm with a fines content of the distribution of 97.1% <1.22 μm.

EXAMPLE 2 a) Preparation of a Uvinul® T 150-containing Aqueous Dispersion 10 g of Uvinul® T 150 were stirred into a solution of 2 g of ascorbyl palmitate in 216 g of acetone. To precipitate out the Uvinul® 150 in colloidally disperse form, this molecularly disperse solution was passed at 20° C. to a mixing chamber where it was mixed with an aqueous solution of 16.88 g of Kollidon 90 F in 1500 ml of demineralized water. The entire process was carried out with a pressure limit of 40 bar in order to prevent evaporation of the solvent. After mixing, a colloidally disperse Uvinul® T 150 dispersion with a white cloudy hue was obtained.

Quasi-elastic light scattering was used to determine the mean particle size as 255 nm with a variance of ±40%. Fraunhofer diffraction was used to determine the mean volume distribution to be D (4.3)=0.62 μm with a fines content of the distribution of 99.8% <1.22 μm.

b) Preparation of a Uvinul® T 150-containing Aqueous Dry Powder

Spray-drying of the dispersion as in 2a) led to a nanoparticulate dry powder. The active ingredient content in the powder was determined by UV/VIS spectroscopy as 21.36% by weight of Uvinul® T 150. The dry powder dissolves in demineralized water to form a white cloudy dispersion (hydrosol).

Quasi-elastic light scattering was used to determine the mean particle size as 350 nm with a variance of ±44%. Fraunhofer diffraction was used to determine the mean volume distribution to be D (4.3)=0.62 μm with a fines content of the distribution of 99.8% <1.22 μm.

EXAMPLE 3

Preparation of a Uvinul® 150-containing Dry Powder With an Active Ingredient Content of 20% by Weight a) Preparation of the Aqueous Dispersion 10 g of Uvinul® T 150 were suspended in a mixture of 166 g of water and 50 g of acetone at room temperature and dissolved to form a molecular solution at a temperature of 240° C. To precipitate out the Uvinul® T 150 in colloidally disperse form, the solution was fed at 240° C. to a mixing chamber where it was mixed with an aqueous solution, adjusted to pH 9.1 using 1 N NaOH, of 16.88 g of gelatin B 100 Bloom and 11.25 g of lactose in 1500 ml of demineralized water. The entire process was carried out with a pressure limit of 40 bar in order to prevent evaporation of the solvent. After mixing, a colloidally disperse Uvinul® T 150 dispersion with a white cloudy hue was obtained.

Fraunhofer diffraction was used to determine the mean volume distribution to be D (4.3)=0.50 μm with a fines content of the distribution of 98.5% <1.22 μm.

b) Preparation of a Uvinal® T150-containing Aqueous Dry Powder

Spray-drying of the dispersion resulted in a dry powder having an active ingredient content of 20.56% by weight of Uvinul® T 150 (content determination by means UV/VIS spectroscopy). The dry powder could be redispersed in demineralized water to form a white cloudy dispersion (hydrosol).

Fraunhofer diffraction was used to determine the mean volume distribution in the redispersion to be D (4.3)=0.65 μm with a fines content of the distribution of 97% <1.22 μm.

EXAMPLE 4

Preparation of a Uvinul® BMBM-containing Dry Powder Having an Active Ingredient Content of 20% by Weight a) Preparation of the Aqueous Dispersion 10 g of Uvinul® BMBM were dissolved in 216 g of acetone at room temperature to give a molecularly disperse solution. To precipitate out the Uvinul® BMBM in colloidally disperse form, the solution was passed at 20° C. to a mixing chamber where it was mixed with an aqueous solution, adjusted to pH 9.1 using 1 N NaOH, of 16.88 g of gelatin B 100 Bloom and 11.25 g of lactose in 1500 ml of demineralized water. The entire process was carried out with a pressure limit of 40 bar in order to prevent evaporation of the solvent. After mixing, a colloidally disperse Uvinul® BMBM dispersion with a white cloudy hue was obtained.

Fraunhofer diffraction was used to determine the mean volume distribution to be D (4.3)=0.50 μm with a fines content of distribution of 98.5% <1.22 μm.

b) Preparation of a Uvinal® BMBM-containing Dry Powder

Spray-drying of the dispersion resulted in a dry powder having an active ingredient content of 20.56% by weight of Uvinul® BMBM (content determination by means of UV/VIS spectroscopy). The dry powder could be redispersed in demineralized water again to form a white cloudly dispersion (hydrosol).

Fraunhofer diffraction was used to determine the mean volume distribution in the redispersion to be D-(4.3)=0.65 μm with a fines content of the distribution of 96.5% <1.20 μm.

EXAMPLE 5

Precipitation of Uvinul® T 150 and Flake Shellac as the Hydrosol, Using Ascorbyl Palmitate and Na Caseinate As active ingredient suspension, 23 g of Uvinul® T 150 and 47 g of flake shellac were firstly stirred into 343 g of isopropanol. As aqueous protective colloid solution, 36 g of Na caseinate and 1.1 g of ascorbyl palmitate were dissolved in 10,820 g of water. The resulting pH was 6.9.

The active ingredient suspension was heated to a temperature of 95° C. and, at a flow rate of 1.1 kg/h, was continuously mixed with isopropanol/water azeotrope, which was brought to a temperature of 218° C., at a flow rate of 0.8 kg/h. Uvinul® T 150 and flake shellac formed a molecular solution. This solution was mixed with the above-mentioned aqueous protective colloid solution, the flow rate of which was 54.8 kg/h. Uvinul® T 150 and flake shellac were precipitated as matrix particles, which were stabilized by Na caseinate as hydrosol. The hydrosol was then concentrated to a solids content of 31% in a rotary evaporator, mixed with 14.6 g of gelatin B 200 Bloom and then worked up by means of double emulsification to give a dry powder. The content of Uvinul® T 150 in the dry powder was then 15%.

Preparations

EXAMPLE 6

| | Lipcare composition Mass content (% by weight) |
|---|---|
| ad 100 | Eucerinum anhydricum |
| 10.00 | glycerol |
| 10.00 | titanium dioxide, micronized |
| 5.00 | Uvinul ® T 150 dry powder from Example 1 |
| 8.00 | octyl methoxycinnamate |
| 5.00 | zinc oxide |
| 4.00 | castor oil |
| 4.00 | pentaerythrityl stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

EXAMPLE 7

| | Composition for sunblock containing micropigments Mass content (% by weight) |
|---|---|
| ad 100 | water |
| 10.00 | octyl methoxycinnamate |
| 6.00 | PEG-7 hydrogenated castor oil |
| 6.00 | titanium dioxide, micronized |
| 5.00 | Uvinul ® T 150 dry powder from Example 1 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

EXAMPLE 8

| | Greasefree gel Mass content (% by weight) |
|---|---|
| ad 100 | water |
| 8.00 | octyl methoxycinnamate |
| 7.00 | titanium dioxide, micronized |
| 5.00 | Uvinul ® T 150 dry powder from Example 1 |
| 5.00 | glycerol |
| 5.00 | PEG-25 PABA |
| 1.00 | 4-methylbenzylidenecamphor |
| 0.40 | acrylates $C_{10}$–$C_{30}$-alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

EXAMPLE 9

| | Sun cream (SPF 20) Mass content (% by weight) |
|---|---|
| ad 100 | water |
| 8.00 | octyl methoxycinnamate |
| 8.00 | titanium dioxide, micronized |
| 6.00 | PEG-7 hydrogenated castor oil |
| 5.00 | Uvinul ® T 150 dry powder from Example 1 |
| 6.00 | mineral oil |
| 5.00 | zinc oxide |
| 5.00 | isopropyl palmitate |
| 0.30 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

EXAMPLE 10

| | Water-resistant sun cream Mass content (% by weight) |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | Uvinul ® T 150 dry powder from Example 1 |
| 4.00 | glycerol |
| 3.00 | jojoba oil |
| 2.00 | 4-methylbenzylidenecamphor |
| 2.00 | titanium dioxide, micronized |
| 1.50 | PEG-45/dodecyl glycol copolymer |
| 1.50 | dimethicone |
| 0.70 | magnesium sulfate |
| 0.50 | magnesium stearate |
| 0.15 | fragrance |

EXAMPLE 11

| | Sun milk (SPF 6) Mass content (% by weight) |
|---|---|
| ad 100 | Water |
| 10.00 | mineral oil |
| 6.00 | PEG-7 hydrogenated castor oil |
| 5.00 | isopropyl palmitate |
| 3.50 | octyl methoxycinnamate |
| 5.00 | Uvinul ® T 150 dry powder from Example 1 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 3.00 | glycerol |
| 0.25 | methylparaben |
| 0.15 | propylparaben |
| 0.05 | tocopherol |

EXAMPLE 12

| | Day lotion with UV protection<br>Mass content (% by weight) |
|---|---|
| ad 100 | water |
| 2.00 | cetearyl alcohol |
| 1.00 | glycerol monostearate |
| 2.00 | vaseline |
| 7.50 | octyl methoxycinnamate |
| 4.00 | octyl salicylate |
| 3.00 | Uvinul ® T 150 dry powder from Example 1 |
| 1.50 | 4-tert-butyl-4'-methoxydibenzoylmethane |
| 0.50 | dimethicone |
| 5.00 | propylene glycol |
| 0.20 | EDTA |
| 0.20 | carbomer |
| 5.00 | $C_{12}$–$C_{15}$-alkyl benzoate |
| 0.27 | triethanolamine |
| 1.00 | tocopheryl acetate |
| q.s. | fragrance |

EXAMPLE 13

| | Day cream with UV protection<br>Mass content (% by weight) |
|---|---|
| ad 100 | water |
| 2.00 | cetearyl alcohol |
| 2.00 | cetyl alcohol |
| 1.00 | glycerol monostearate |
| 2.00 | vaseline |
| 7.50 | octyl methoxycinnamate |
| 4.00 | octyl salicylate |
| 3.00 | Uvinul ® T 150 dry powder from Example 1 |
| 1.50 | 4-tert-butyl-4'-methoxydibenzoylmethane |
| 4.00 | propylene glycol |
| 0.20 | EDTA |
| 0.20 | carbomer |
| 0.20 | xanthan |
| 0.20 | $C_{10}$–$C_{30}$-alkyl acrylate crosspolymer |
| 5.00 | $C_{12}$–$C_{15}$-alkyl benzoate |
| 0.54 | triethanolamine |
| 1.00 | tocopheryl acetate |
| q.s. | fragrance |
| q.s. | preservative |

EXAMPLE 14

| | Liquid foundation<br>Mass content (% by weight) |
|---|---|
| ad 100 | water |
| 2.00 | cetearyl alcohol |
| 2.00 | ceteareth 25 |
| 6.00 | glycerol monostearate |
| 1.00 | cetyl alcohol |
| 8.00 | paraffin oil |
| 7.00 | cetearyl octanoate |
| 0.2 | dimethicone |
| 3.00 | propylene glycol |
| 1.00 | panthenol |
| 3.00 | Uvinul ® T 150 dry powder from Example 1 |
| 1.50 | 4-tert-butyl-4'-methoxydibenzoylmethane |
| 3.50 | octyl methoxycinnamate |
| 0.1 | bisabolol |
| 5.70 | titanium dioxide |
| 1.10 | iron oxide |
| q.s. | fragrance |

EXAMPLE 15

| | Hair gel with sun protection<br>Mass content (% by weight) |
|---|---|
| ad 100 | water |
| 1.20 | carbomer |
| 0.50 | hydroxyethylcellulose |
| 4.00 | triethanolamine |
| 0.70 | PEG-40 hydrogenated castor oil |
| 1.50 | Uvinul ® T 150 dry powder from Example 1 |
| 0.70 | 4-tert-butyl-4'-methoxydibenzoylmethane |
| 2.80 | octyl methoxycinnamate |
| 5.00 | propylene glycol |
| 0.01 | EDTA |
| q.s. | fragrance |
| q.s. | Sicovit Patentblau 85 E 131 |

We claim:

1. An aqueous dispersion of sparingly water-soluble or water-insoluble organic UV filter substances, which comprises at least one sparingly water-soluble or water-insoluble organic UV filter substance as colloidally disperse phase in amorphous or partially amorphous form, wherein the at least one sparingly water-soluble or water-insoluble organic UV filter substance is a 1,3,5-triazine derivative of the formula I

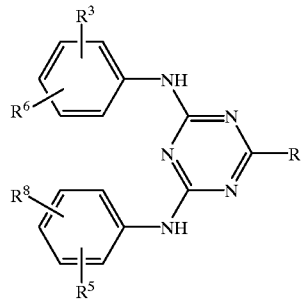

in which the substituents independently of one another have the following meanings:

R is hydrogen, halogen, OH, $C_1$–$C_{20}$-alkyl, $C_1$–$C_{20}$-alkoxy, $C_1$–$C_{20}$-alkoxyalkyl, $C_1$–$C_{20}$-hydroxyalkoxy, $NR^1R^2$, or a radical of the formula Ia

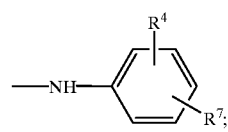

$R^1$ and $R^2$
are hydrogen, $C_1$–$C_{20}$-alkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl;

$R^3$ to $R^5$
are hydrogen, OH, $NR^9R^{10}$, $C_1$–$C_{20}$-alkoxy, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl;

$R^6$ to $R^8$ are hydrogen, $C_1$–$C_{20}$-alkoxy, —C(=O)—$R^{11}$, —C(=O)—X—$R^{12}$, $SO_2R^{13}$, CN $R^9$ to $R^{11}$ are hydrogen, $C_1$–$C_{20}$-alkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl;

$R^{12}$ is hydrogen, $C_1$–$C_{20}$-alkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl or a radical of the formula Sp-Sil;

$R^{13}$ is $C_1$–$C_{20}$-alkyl, $C_5$–$C_8$-cycloalkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl;

X is O, $NR^{14}$;

$R^{14}$ is hydrogen, $C_1$–$C_{20}$-alkyl, $C_6$–$C_{12}$-aryl optionally substituted by one or more $C_1$–$C_4$-alkyl, $C_7$–$C_{10}$-aralkyl optionally substituted by one or more $C_1$–$C_4$-alkyl, heteroaryl optionally substituted by one or more $C_1$–$C_4$-alkyl, $C_5$–$C_8$-cycloalkyl;

Sp is a spacer;

Sil is a radical from the group consisting of silanes, oligosiloxanes and polysiloxanes.

2. An aqueous dispersion as claimed in claim 1, which is a suspension which comprises at least one sparingly water-soluble or water-insoluble organic UV filter substance as nanoparticulate particles in amorphous or partially amorphous form.

3. An aqueous dispersion as claimed in claim 1, wherein the particles of the colloidally disperse phase have a core and a shell, where the core comprises at least one sparingly water-soluble or water-insoluble organic UV filter substance, and the shell comprises at least one protective colloid.

4. An aqueous dispersion as claimed in claim 1 wherein the particles of the colloidally disperse phase have a mean particle size of less than 10 μm.

5. An aqueous dispersion as claimed in claim 1 comprising 0.1 to 70% by weight of at least one sparingly water-soluble or water-insoluble organic UV filter subtance, 0.1 to 80% by weight of at least one polymeric protective colloid, all of the percentages being based on the dry mass of the aqueous dispersion.

6. An aqueous dispersion as claimed in claim 5, additionally comprising 0.1 to 70% by weight of at least one softener, 0.01 to 70% by weight of at least one emulsifier and/or 0.01 to 50% by weight of at least one antioxidant and/or preservative.

7. An aqueous dispersion as claimed in claim 1, wherein the particles of the colloidally disperse phase comprise a water-insoluble polymer matrix into which at least one sparingly water-soluble or water-insoluble organic UV filter substance has been embedded.

8. An aqueous dispersion as claimed in claim 7, wherein the colloidally disperse particles have additionally been coated by a protective colloid.

9. An aqueous dispersion as claimed in claim 7, comprising 0.1 to 70% by weight of at least one sparingly water-soluble or water-insoluble organic UV filter substance, 0.1 to 80% by weight of at least one water-insoluble matrix polymer and 0 to 80% by weight of at least one polymeric protective colloid, all of the percentages being based on the dry mass of the aqueous dispersion.

10. An aqueous dispersion as claimed in claim 9, additionally comprising 0.1 to 70% by weight of at least one softener, 0.01 to 70% by weight of at least one emulsifier and/or 0.01 to 50% by weight of at least one antioxidant.

11. An aqueous dispersion as claimed in claim 1, comprising at least one 1,3,5-triazine derivative of the formula Ib in which the substituents, independently of one another, have the following meanings:

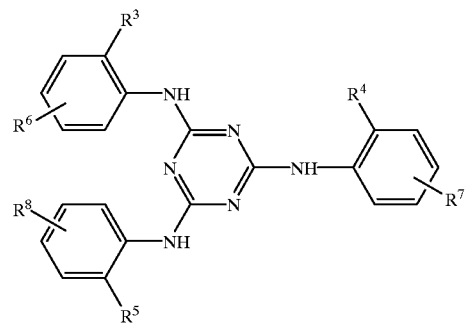

Ib $R^3$ to $R^5$ are hydrogen, OH;

$R^6$ to $R^8$ are $C_1$–$C_{12}$-alkoxy, —C(=O)—X—$R^{12}$;

X is O, $NR^{14}$;

$R^{12}$ and $R^{14}$ are hydrogen, $C_4$–$C_8$-alkyl.

12. A process for the preparation of an aqueous dispersion of at least one sparingly water-soluble or water-insoluble organic UV filter substance, defined as in claim 1, which comprises a) preparing a molecularly disperse solution of at least one sparingly water-soluble or water-insoluble organic UV filter substance in an organic solvent, b) treating this solution with an aqueous solution of at least one protective colloid, the hydrophobic phase of the UV filter substance forming as colloidally disperse phase, and c) freeing the resulting dispersion from the organic solvent.

13. A process as claimed in claim 12, wherein the organic solvent used in process step a) is at least one water-miscible, organic solvent or a mixture of water and at least one water-miscible organic solvent.

14. A process as claimed in claim 12, wherein further additives, chosen from the group consisting of emulsifiers, antioxidants, preservatives, water-insoluble polymers and cosmetic oils are added to the molecularly disperse solution in step a).

15. A process as claimed in claim 12, wherein, in step b), the aqueous protective colloid solution additionally comprises at least one softener.

16. A process as claimed in claim 12, wherein, in step a), the molecularly disperse solution of at least one sparingly water-soluble or water-insoluble organic UV filter substance is prepared at temperatures greater than 15° C., and immediately thereafter, is treated in step b) with the aqueous solution of the protective colloid, a mixing temperature of from 35° C. to 120° C. being established.

17. A process for the preparation of an aqueous dispersion of at least one sparingly water-soluble or water-insoluble organic uv filter substance, defined as in claim 7, which comprises
   a) preparing a molecularly disperse solution of at least one sparingly water-soluble or water-insoluble organic UV filter substance and a water-insoluble polymer in an organic solvent,
   b) treating this solution with water or an aqueous solution of at least one protective colloid, the hydrophobic phase of the mixture comprising UV filter substance and water-insoluble polymer forming as colloidally disperse phase, and
   c) freeing the resulting dispersion from the organic solvent.

18. A process as claimed in claim 17, wherein, in step b), an aqueous protective colloid solution is used.

19. A process for the preparation of a dry powder comprising at least one sparingly water-soluble or water-insoluble organic UV filter substance as nanoparticular particles in amorphous or partially amorphous form, which comprises freeing an aqueous dispersion defined as in claim 1 from the water and drying it, optionally in the presence of a coating material.

20. A pulverulent preparation of at least one sparingly water-soluble or water-insoluble organic filter substance obtainable by a process defined as in claim 19, comprising at least one sparingly water-soluble or water-insoluble organic UV filter substance as nanoparticular particles in amorphous or partially amorphous form.

21. A process for the preparation of an oil-miscible preparation of at least one sparingly-water-soluble or water-insoluble organic UV filter substance in the form of a double dispersion, which comprises emulsifying an aqueous dispersion defined as in claim 1 in the presence of an emulsifier in oil.

22. A liquid, oil-miscible preparation of at least one sparingly water-soluble or water-insoluble organic UV filter substance obtainable by a process defined as in claim 21, which, as a double dispersion system, comprises an aqueous-disperse phase having a particle diameter of less than 500 $\mu$m, in which protective-colloid-stabilized particles of one or more sparingly water-soluble or water-insoluble organic UV filter substances are present in dispersed form, in an oil as dispersant.

23. A process for protecting organic materials from UV light damage comprising applying or incorporating the aqueous dispersion defined as in claim 1 onto or into the organic materials.

24. A process for protecting organic materials from UV light damage comprising applying or incorporating the pulverulent preparation defined as in claim 23 onto or into the organic materials.

25. A process for protecting organic materials from UV light damage comprising applying or incorporating the liquid, oil-miscible preparation defined as in claim 22 or into the organic materials.

26. The process as claimed in claim 23, wherein the organic materials are selected from the group consisting of plastics and coating materials.

27. The process as claimed in claim 23, wherein the aqueous dispersion is incorporated into cosmetic and pharmaceutical preparations for protecting human skin or human hair from UV rays, and the preparations are applied to the human skin or human hair.

28. The process use as claimed in claim 23, wherein the aqueous dispersion is incorporated into cosmetic and pharmaceutical preparations.

29. A cosmetic or pharmaceutical preparation comprising a light protection agent for protecting the human skin or human hair from UV light in the range from 280 to 400 nm, which comprises, as photostable UV filter, an effective amount of an aqueous dispersion defined as in claim 1 in a cosmetically or pharmaceutically suitable carrier.

30. A cosmetic or pharmaceutical preparation comprising a light protection agent for protecting the human skin or human hair from UV light in the range from 280 to 400 nm, which comprises, as photostable UV filter, an effective amount of a pulverulent preparation defined as in claim 20 in a cosmetically or pharmaceutically suitable carrier.

31. A cosmetic or pharmaceutical preparation comprising a light protection agent for the protection of human skin or human hair against UV light in the range from 280 to 400 nm, which comprises, as photostable UV filter, an effective amount of a liquid, oil-miscible preparation defined as in claim 22 in a cosmetically or pharmaceutically suitable carrier.

* * * * *